United States Patent
Semet

(10) Patent No.: US 7,621,913 B2
(45) Date of Patent: Nov. 24, 2009

(54) INTERLOCKING INTRAMEDULLARY NAILS WITH OUTER SCREW

(76) Inventor: Elliot Charles Semet, 403 Osprey Pt. Dr., Brielle, NJ (US) 08730

(\*) Notice: Subject to any disclaimer, the term of this patent is extended or adjusted under 35 U.S.C. 154(b) by 390 days.

(21) Appl. No.: 11/803,456

(22) Filed: May 16, 2007

(65) Prior Publication Data
US 2007/0260247 A1 Nov. 8, 2007

Related U.S. Application Data

(62) Division of application No. 10/816,674, filed on Apr. 2, 2004, now abandoned.

(60) Provisional application No. 60/459,952, filed on Apr. 4, 2003.

(51) Int. Cl.
*A61F 2/30* (2006.01)

(52) U.S. Cl. .................................. 606/62; 606/96

(58) Field of Classification Search .................... 606/53, 606/60, 62–68, 86 R, 95–98; *A61B 17/56, A61B 17/58; A61F 2/30*
See application file for complete search history.

(56) References Cited

U.S. PATENT DOCUMENTS 5,454,813 A \* 10/1995 Lawes .......................... 606/62
7,347,861 B2 \* 3/2008 Johnstone .................... 606/62

\* cited by examiner

*Primary Examiner*—Eduardo C Robert
*Assistant Examiner*—Lynnsy Schneider
(74) *Attorney, Agent, or Firm*—Arthur M. Peslak, Esq.; Mandel & Peslak, LLC

(57) ABSTRACT

A new method for locking Intramedullary Nails (IM Nails) using a headless screw for performing interlocking with the nail. A subsequent, canulated outer screw is placed in such a way that it encapsulates this headless screw. The outer screw locks to the IM Nail and holds the headless screw in place to eliminate play in the screw-nail interface and results in a more stable form of fixation.

1 Claim, 3 Drawing Sheets

INTERLOCKING INTRAMEDULLARY NAILS WITH OUTER SCREW

CROSS REFERENCE TO RELATED APPLICATIONS

This is a division of application Ser. No. 10/816,674 filed Apr. 2, 2004 now abandoned which claimed priority to U.S. Provisional Patent Application No. 60/459,952 filed Apr. 4, 2003.

BACKGROUND OF THE INVENTION

The present invention is directed to the field of orthopedic surgery. In particular, the present invention is directed to a new method for fracture reduction.

The currently available methods of fracture reduction are:
Casts/Braces
Plates:
  Conventional
  Locking
External Fixation
Intramedullary Nails
Intramedullary nails have several advantages over other forms of fixation:
They are less invasive than plates;
They have a lower infection rate;
Nails are stronger than plates;
Nails have a mechanical advantage compared to plates;
The screws used with nails are more resistant to breakage due to the decreased moment arm;
Nails have a high rate of union;
Nails allow for anatomic alignment;
Casts/braces immobilize the limb and do not allow early motion; and
External fixators have a risk of pin tract infections.

One of the currently available methods of interlocking IM Nails is to solely use screws, which can result in loss of reduction because of the inherent play in the screw-nail interface. A second method of interlocking IM Nails is to cap the screw at the contra lateral cortex, which increases fixation in the cortical bone. However, this method does not help the screw-nail interface. Additionally, pressure applied by the capping on one end may cause the distal end to move out of position. A third available method of interlocking IM Nails is to have the hole of the IM Nail lined with rubber to provide a more grippable material for the screws. However the inherent play in rubber does not provide sufficient locking. The rubber-lined IM Nails also suffer from the disadvantage of the possibility for foreign body reactions if flaking of the rubber occurs.

The method of the present invention, with a threaded guidewire in between the screws, locks the screw in place, eliminates play, and results in a more stable form of fixation of a fracture.

Two other patented methods of interlocking IM Nails were found, however, neither are currently marketed:

An interlocking Intramedullary Nail (U.S. Pat. No. 6,524, 314, granted Feb. 25, 2003) provides for a different mechanism, using 2 lag screws and a locking screw. This product is currently not marketed but would be a difficult mechanism because there are only a couple of safe zones where the screws can be placed. With the addition of two screws placed for fixation, it may be difficult to find safe zones. Additionally, the screws may cross thread early prohibiting further insertion.

An interlocking Intramedullary Nail (U.S. Pat. No. 6,019, 761, granted Feb. 1, 2000) provides for interlocking by placing a guidewire through one screw hole up to and out of the next. This patent also relies on drilling holes versus already manufactured holes and dropping wires through the holes and using the screws to cause the wires to interlock to the screws. This patent has a completely different means by which the interlocking would occur and be enhanced.

This new mechanism, with the headless screw and outer screw, locks the screw in place to eliminate this play and result in a more stable form of fixation. A sleeve on the outer end of the screw will aid in the centering of the screw. Additionally, the option of placing an outer screw on both sides of the IM Nail offers a possibly stronger fixation with increased ability to center the IM Nail.

BRIEF SUMMARY OF THE INVENTION

Figure 1:
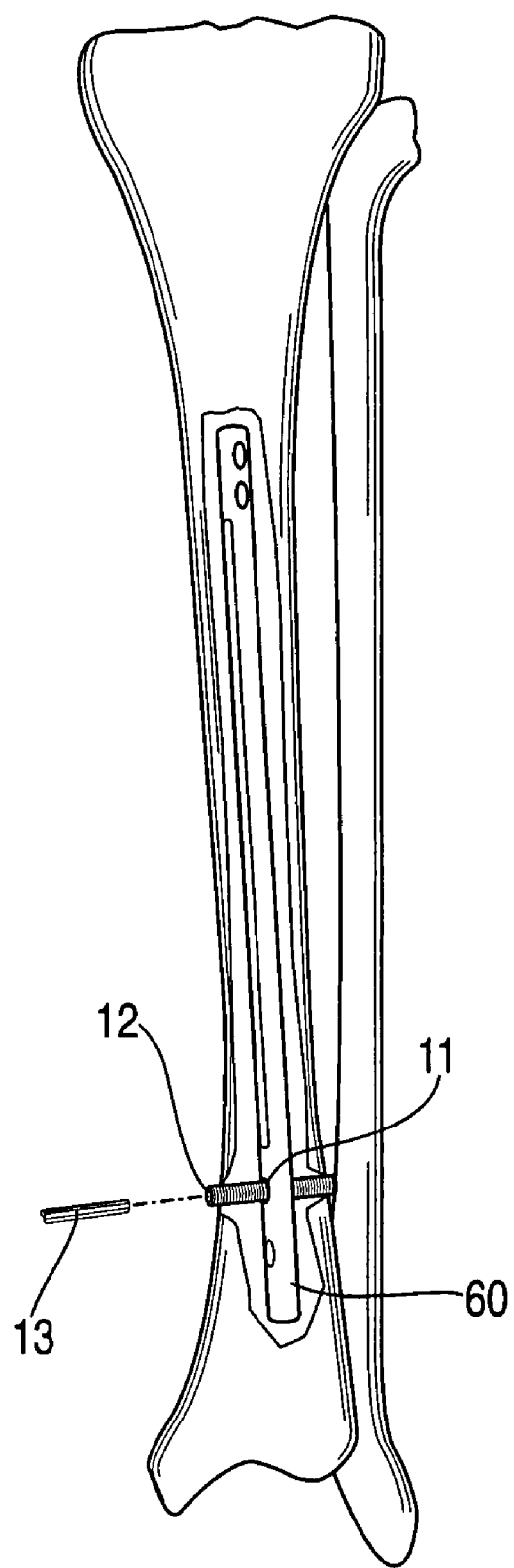
FIG. 1 is a sectional view of the insertion of the first headless screw into the IM Nail.
Figure 2:
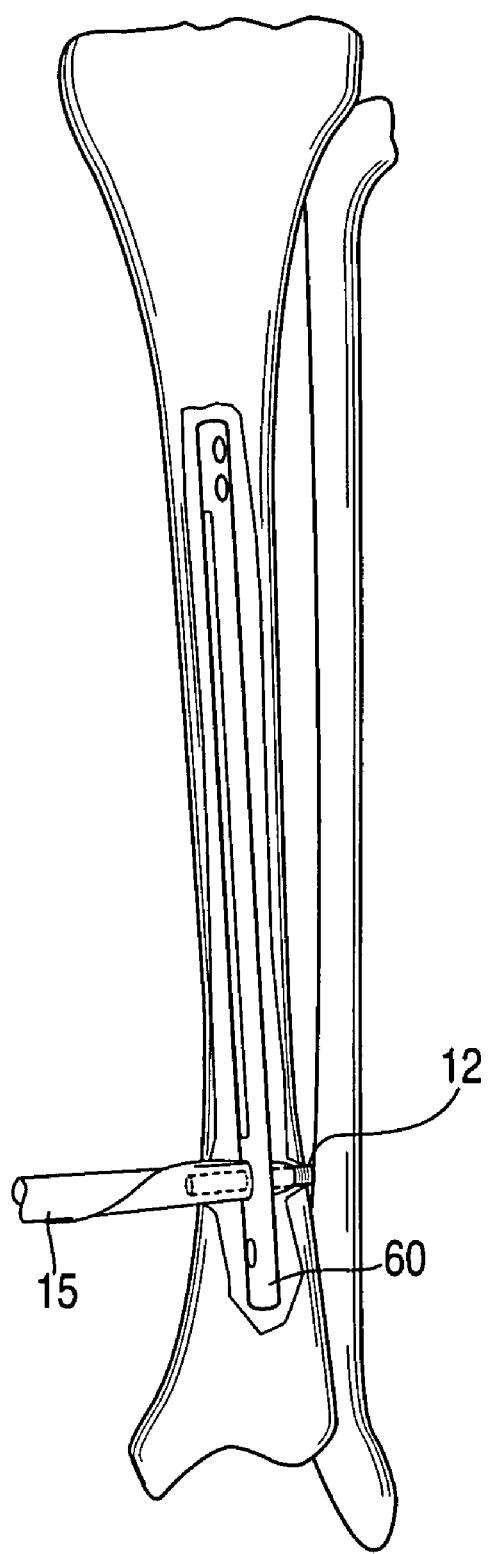
FIG. 2 is a section view illustrating the over drilling around the headless screw with the canulated drill.
Figure 3:
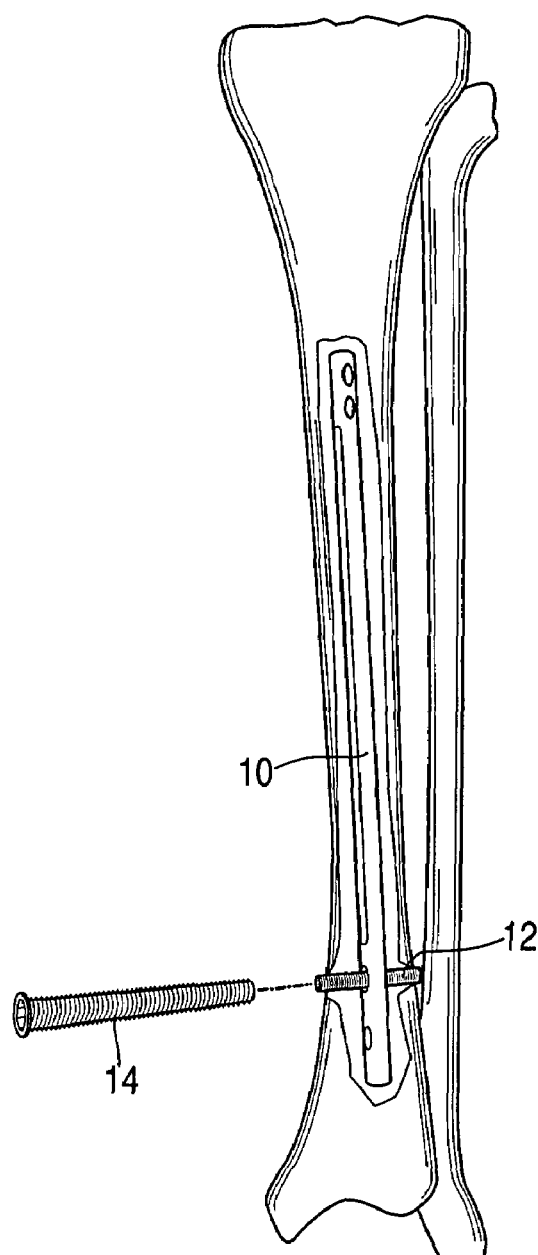
FIG. 3 is a sectional view illustrating the insertion of the outer screws to the inner screw and IM Nail.
Figure 4:
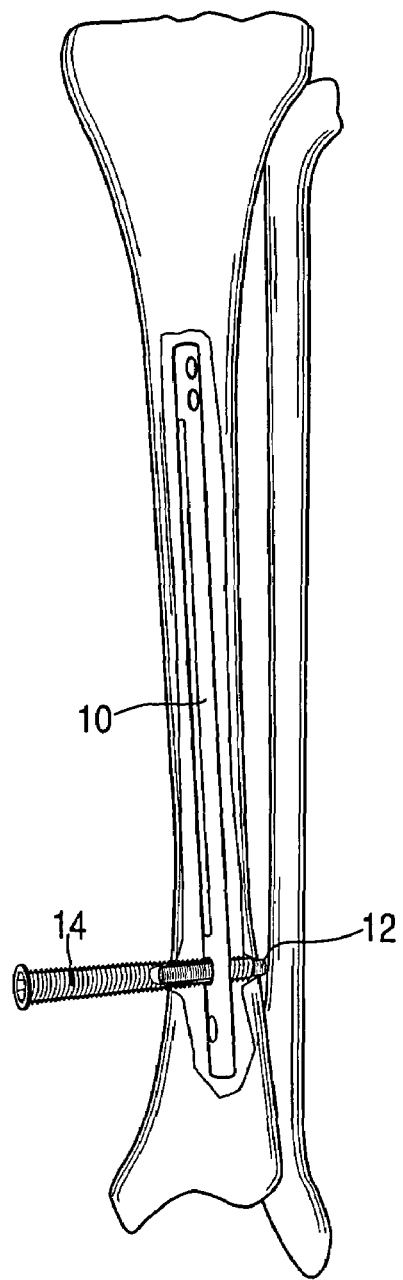
FIG. 4 is a sectional view illustrating the interlocking of the outer screws to the inner screw and IM Nail.

This invention provides for a new method for locking Intramedullary Nails (IM Nails) with headless screws for performing interlocking with the IM Nail. The headless screw is over drilled with a canulated drill. A subsequent, outer screw, is placed such that it encapsulates this headless screw. The outer screw engages threads on the IM Nail, locking the outer screw to the nail. This method and design eliminates play in the screw-nail interface and results in a more stable form of fixation. The headless screw may also have a sleeve on the outer end, which will aid in centering of the IM Nail. The outer screw may also be placed from the contra lateral side where the anatomy will allow it.

DETAILED DESCRIPTION OF THE PRESENT INVENTION

The IM Nails and screws are manufactured with cobalt-chrome, titanium or other materials for strength and durability. The currently available methods do not address screw-nail interface locking and can cause loss in reduction. In the present invention, the IM Nail 10 is secured by headless screws 12 and canulated outer screws 14 that cap the headless screws 12. The present invention thus secures and eliminates movement of the screws relative to the IM Nail 10.

The screwdriver 13, which is normally an Allen key for placing the headless screw 12 remains attached to the headless screw 12 after insertion. A decision by the surgeon is made on the length of the outer screw 14 (the one that encapsulates the headless screw 12) to be placed so that the IM Nail 10 is kept at a fixed distance from the cortex of the bone. The headless screw 14 is then over drilled with a canulated drill 15. The outer screw 14 is then placed over the screwdriver 13 and then over the headless screw 12. The outer screw 14 engages threads 11 on the intramedullary nail 10, locking the outer screw 14 to the IM Nail 10. The opening of the IM Nail 10 may be tapered such that it allows the outer screw 14 a perpendicular insertion to the intramedullary nail 10. The screw 14 may also be tapered such that that it can also interlock with the IM Nail 10.

Additionally, a small thin sleeve may be on the outer screw 14 that will allow for centering the headless screw in the nail opening. This will eliminate the play of the headless screw 12 within the nail 10. Upon a surgeon's discretion, a similar outer screw 14 can be placed from the contra lateral side where the anatomy will allow it.

Currently available methods of interlocking IM Nails do not eliminate play in the screw-nail interface. Therefore, current methods can result in loss of reduction of the fracture. The present invention eliminates play in the screw-nail interface and results in a more stable form of fixation.

The invention claimed is:

1. A method for securing an intramedullary nail to a fractured bone comprising the steps of:
   (a) Inserting a headless screw into the intramedullary nail;
   (b) Tightening the headless screw to the intramedullary nail by means of a screwdriver that remains in place after tightening;
   (c) Inserting a canulated drill bit over the headless screw;
   (d) Using the canulated drill bit to create threads on the inside of the intramedullary nail;
   (e) Inserting a second screw over the screwdriver and headless screw and tightening the second screw to the threads on the inside of the intramedullary nail; and
   (f) Repeating steps a to e contra laterally as necessary until the intramedullary nail is secured to the fractured bone.

* * * * *